United States Patent

Mai et al.

[11] Patent Number: 4,551,537
[45] Date of Patent: Nov. 5, 1985

[54] SYNTHESIS OF ALPHA-AMINONITRILES

[75] Inventors: Khuong H. X. Mai; Ghanshyam Patil, both of Vernon Hills, Ill.

[73] Assignee: American Hospital Supply Corporation, Evanston, Ill.

[21] Appl. No.: 654,429

[22] Filed: Sep. 26, 1984

[51] Int. Cl.[4] .................. C07D 213/55; C07C 121/78
[52] U.S. Cl. .............................. 546/330; 260/465 D; 260/465 E; 548/561; 549/74; 549/492; 556/417
[58] Field of Search ...................... 260/465 E, 465 D; 556/417; 546/330; 548/561; 549/74, 492

[56] References Cited

PUBLICATIONS

Stout et al., J. Org. Chem., vol. 48, 5369, (1983).

Primary Examiner—Dolph H. Torrence
Attorney, Agent, or Firm—Gildo E. Fato

[57] ABSTRACT

Disclosed is a process for preparing optically active alpha-aminonitriles of the formula

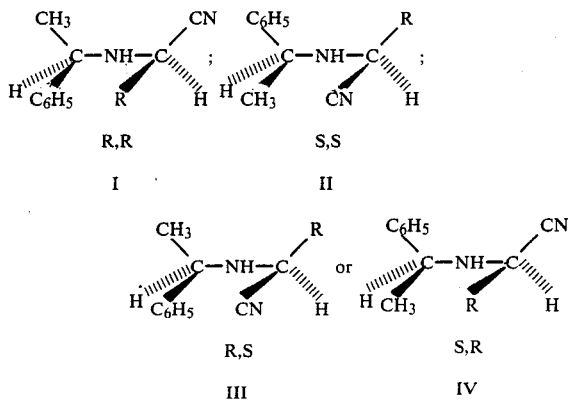

by the reaction of alpha-trimethylsilyloxynitriles with optically active alpha-methylbenzylamine in the presence of a loweralkyl alcohol.

In the above formula, R denotes $C_1$–$C_{20}$ alkyl, $C_3$–$C_{12}$ cycloalkyl, $C_7$–$C_{15}$ aralkyl or unsubstituted or substituted aryl or heteroaryl.

In general, R-alpha-methylbenzylamine gave I and III as the major and the minor products, respectively. Whereas, S-alpha-methylbenzylamine gave II and IV as the major and the minor products, respectively.

The compounds so prepared are intermediates in the preparation of optically active aminoacids.

5 Claims, No Drawings

SYNTHESIS OF ALPHA-AMINONITRILES

BACKGROUND OF THE INVENTION

The preparation of optically active alpha-aminonitriles is the key step in the preparation of many aminoacids. See for example the publications by K. Harada or Harada et al in J. ORG. CHEM. 31, 1956 (1966); 32, 1790 (1967); 32, 1794 (1967; 33, 4526 (1968); NATURE 200, 1201 (1963); or NATURWISS 51, 106 (1964). In general, most of the reported methods disclose either the reaction of optically active alpha-methylbenzylamine with a racemic cyanohydrin (NATURE 200, 1201 or NATURWISS 51, 106) or the addition of hydrogen cyanide gas to an optically active Schiff base (M. Patel et al CAN. J. CHEM. 48, 1881, 1970). Ojima et al, CHEM. LETT. 331, 737 (1975), have shown that trimethylsilyl cyanide (TMSCN) reacts with aldimines in the presence of a catalytic amount of $AlCl_3$ to give N-TMS-alpha-aminonitriles. Stout et al have recently reported the direct preparation of optically active aminonitriles from aldehydes (J. ORG. CHEM. 48, 5369, 1983).

SUMMARY OF THE INVENTION

In accordance with the present invention, disclosed is a process for preparing optically active alpha-aminonitriles of the formula

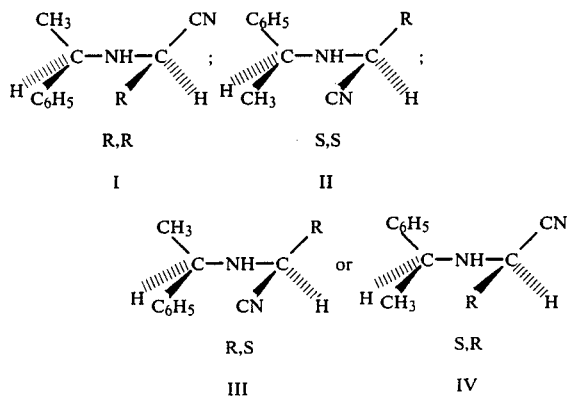

by the reaction of alpha-trimethylsilyloxynitriles with optically active alpha-methylbenzylamine in the presence of a loweralkyl alcohol such as methanol, ethanol, n-propyl or isopropyl alcohol, n-butyl, isobutyl or t-butyl alcohol, pentanol or hexanol.

In the above formula, R denotes $C_1-C_{20}$ alkyl, $C_3-C_{12}$ cycloalkyl, $C_7-C_{15}$ aralkyl or unsubstituted or substituted aryl or heteroaryl.

The term "alkyl" as used herein refers to straight or branched chain alkyl radicals containing from 1 to 20 carbon atoms including but not limited to methyl, ethyl, n-propyl,; iso-propyl, n-butyl, sec-butyl, t-butyl, 2-methylhexyl, n-pentyl, 1-methylbutyl, 2,2-dimethylbutyl, 2-methylpentyl, 2,2-dimethylpropyl, n-hexyl, heptyl, octyl, nonyl, decyl or dodecyl and the like.

The term "cycloalkyl" as used herein refers to cyclic saturated aliphatic radicals containing 3 to 12 carbon atoms in the ring, such as cyclopropyl, cyclobutyl, cyclopentyl, cyclohexyl, cyclooctyl.

The term "halo" includes chloro, fluoro, bromo and iodo.

The term "aryl" represents phenyl or naphthyl which may be unsubstituted or substituted with loweralkyl of from one to about 6 carbon atoms, halo, hydroxy, amino, nitro, lower alkoxy, carboxy lower alkanoyl, or lower alkoxycarbonyl.

The term "heteroaryl" represents heterocyclic ring systems of 5 to 6 membered groups such as pyridyl, thienyl, furyl or pyrrolyl.

DETAILED DESCRIPTION OF THE INVENTION

In accordance with the present invention, one embodiment of the invention comprises the asymmetric synthesis of alpha-aminonitriles via the amination of alpha-silyloxynitriles with optically active alpha-methylbenzylamine in methanol as depicted by the following reaction scheme. For a further description of the preparation of alpha-aminonitriles, reference can be made to co-pending application Ser. No. 654,430,

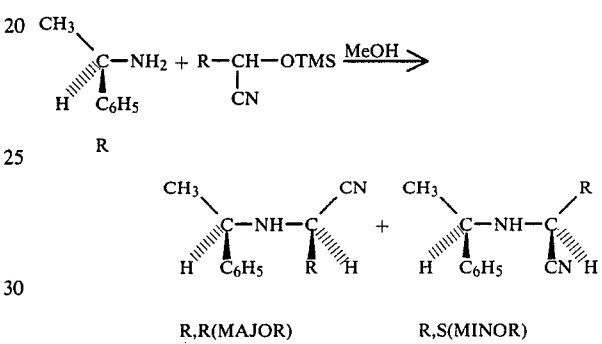

In general, it has been found that the R rotamer of alpha-methylbenzylamine produced the corresponding RR-aminonitrile as the major product, whereas the S rotamer provided its SS-counterpart. The major diastereomer could be isolated in its optically pure form by multiple recrystallizations. The minor diastereoisomers RS and SR are also produced.

In a typical procedure, a mixture of aldehyde (50 mmol), TMSCN (60 mmol) and a catalytic amount of $ZnI_2$ was stirred for 15 minutes and was added to a solution of (R)-alpha-methylbenzylamine (40 mmol) in methanol (30 ml). The mixture was then refluxed with stirring for 2 hours, and evaporated in vacuo. The residue was taken up with ether, dried over $MgSO_4$, and filtered. Gaseous HCl was bubbled through the filtrate and the precipitated solid was collected by filtration. The crude solid was a mixture of a major (RR) and a minor (RS) diastereomer. This was repeatedly (usually twice) recrystallized from methanol-ether until H NMR showed the disappearance of the minor diastereoisomer. The reaction temperature is 0° C. to about 125° C., preferably 25° to 75° C. and the reaction time is several minutes to 24 hours, preferably 5 minutes to 2 hours.

In a similar manner, aliphatic, aromatic and heteroaromatic alpha-aminonitriles were prepared.

EXAMPLE I (−)-alpha-(alpha-Methylbenzyl)aminophenylacetonitrile hydrochloride To a mixture of benzaldehyde (4.25 g; 0.04 m) and trimethylsilyl cyanide (5 g, 0.05 m) was added a catalytic amount of zinc iodide. After the exothermic reaction subsided, methanol (30 ml) was added to destroy any excess trimethylsilyl cyanide, and (+)-(R)-(1- methylbenzyl)amine (3.6 g; 0.03 m) was added. The mixture was then refluxed for 2.5 hours, and evaporated in vacuo. The residue was taken up in ether and filtrate. A stream of hydrogen chloride gas was bubbled through the filtrate. The supernatant layer was decanted and the residue was washed several times with ether. The crude solid residue (8.3 g) which consisted of 2 diastereoisomers (R,R and R,S; 3.3:1) was recrystallized twice from methanol-ether to afford the optically pure R,R-isomer of alpha-(alpha-methylbenzyl)amino-phenylacetonitrile hydrochloride, 2.7 g (25%), m.p. 152°-156° C., $[alpha]_D + 69.2°$ (C=1.0, MeOH). NMR and IR data were consistent with the assigned structure.

In an analogous manner to the procedure described in Example 1, compounds of formula I substituted as set forth in Table 1, were prepared.

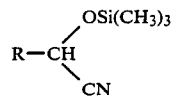

with an optically active compound of the formula

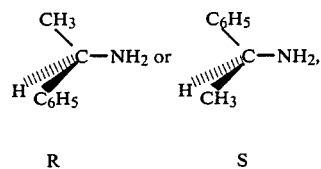

R           S

TABLE I

R,R Diastereomeric Alpha-aminonitriles

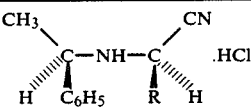

| R | Ratio of Diastereomers[a] (RR:RS) | Total Yield % | Isolated Yield of R,R Diastereomer %[b] | [Alpha] deg[c] | Mp, °C. |
|---|---|---|---|---|---|
| CH$_3$ | 3.3:1 | 95 | 22 | +102.6 | 145-8 |
| C$_2$H$_5$ | 3.2:1 | 92 | 10 | +97.5 | 140-5 |
| C$_6$H$_5$ | 3.0:1 | 97 | 25 | +69.2 | 152-6 |
| 2-MeOC$_6$H$_4$ | 2.8:1 | 91 | 15 | +91.0 | 138-43 |
| 2-ClC$_6$H$_4$ | 5.7:1 | 90 | 72 | +117.1 | 155-7 |
| 4-ClC$_6$H$_4$ | 3.6:1 | 92 | 47 | +46.7 | 145-51 |
| 4-MeC$_6$H$_4$ | 3.4:1 | 98 | 40 | +56.7 | 145-50 |
| 4-MeOC$_6$H$_4$ | 2.8:1 | 95 | 35 | +44.9 | 125-7 |
| 4-MeSC$_6$H$_4$ | 3.8:1 | 91 | 56 | +34.8 | 144-6 |
| 2-Thienyl | 2.9:1 | 90 | 36 | +52.4 | 132-3 |
| 4-HO—3,5-(t-Bu)$_2$C$_6$H$_5$ | 1.0:0[d] | 97 | 97 | +22.8 | 173-5 |

[a]Based on the NMR integration of the alpha-proton.
[b]All compounds had elemental analyses within +0.4% of the theoritical values.
[c]Taken in methanol, c 1.
[d]When the free base of this compound was dissolved in ether and acidified with gaseous HCl, no precipitation was observed. Upon standing overnight, crystals of the R,R diastereomer slowly separated and were identified as the only component.

Absolute configuration and optical purity of the products were determined on the basis of $^1$H NMR using literature methods. In general, the chemical shift of the R,R-diastereomeric-alpha-H is about 0.2 to 0.5 up field as compared to its R,S counterpart.

What is claimed is:

1. A process for preparing an optically active compound of the formula

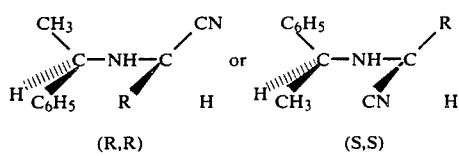

wherein R is C$_1$–C$_{20}$ alkyl, C$_3$–C$_{12}$ cycloalkyl, C$_7$–C$_{15}$ aralkyl or a phenyl or naphthyl group which may be unsubstituted or substituted with loweralkyl of from 1 to about 6 carbon atoms, halo, hydroxy, amino, nitro, lower alkoxy, carboxy lower alkanoyl, or lower alkoxycarbonyl, or a pyridyl, thienyl, furyl or pyrrolyl group, which process comprises: reacting in an inert medium, a compound of the formula respectively at a temperature and for a time sufficient to complete the reaction between said compounds.

2. The method of claim 1 wherein a compound of the formula

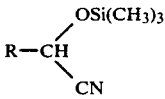

is reacted with the optically active compound

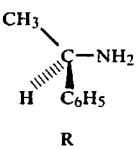

to produce the minor diastereoisomer

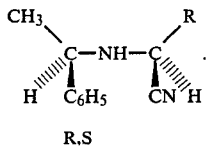

R,S

3. The method of claim 1 wherein a compound of the formula

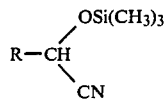

is reacted with the optically active compound

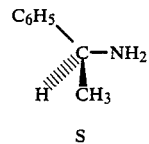

S to produce the minor diastereoisomer

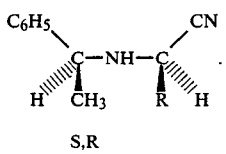

S,R

4. The process of claim 1 wherein the compound

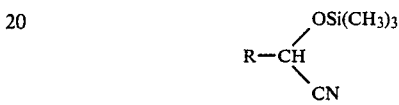

is reacted with the optically active compound at a temperature of from 0° C. to about 125° C. for a time up to about 24 hours.

5. The process of claim 4 wherein the reaction is conducted at a temperature of about 25° C. to about 125° C. for a time of about 30 minutes to about 2 hours.

* * * * *